United States Patent
Berra

(10) Patent No.: US 8,001,846 B2
(45) Date of Patent: Aug. 23, 2011

(54) MOBILE TESTING DEVICE AND METHOD OF USING THE DEVICE

(75) Inventor: Victor Berra, Comodoro Rivadavia (AR)

(73) Assignee: Petroil S.R.L., Comodoro Rivadavia (AR)

( * ) Notice: Subject to any disclaimer, the term of this patent is extended or adjusted under 35 U.S.C. 154(b) by 275 days.

(21) Appl. No.: 12/026,951

(22) Filed: Feb. 6, 2008

(65) Prior Publication Data

US 2008/0184808 A1   Aug. 7, 2008

(30) Foreign Application Priority Data

Feb. 6, 2007  (AR) ................................. P070100491
Nov. 20, 2007 (BO) ........................................ 270422

(51) Int. Cl.
  *G01N 3/08* (2006.01)
(52) U.S. Cl. ......................................................... 73/828
(58) Field of Classification Search ...................... 73/828
  See application file for complete search history.

(56) References Cited

U.S. PATENT DOCUMENTS

| | | | | |
|---|---|---|---|---|
| 2,255,061 A | * | 9/1941 | Johnson | 172/799.5 |
| 2,595,864 A | * | 5/1952 | Lowry | 212/181 |
| 3,083,837 A | * | 4/1963 | Jones et al. | 212/295 |
| 3,445,004 A | * | 5/1969 | Grider et al. | 212/349 |
| 5,340,187 A | * | 8/1994 | Haddad, Jr. | 296/98 |
| 5,586,667 A | * | 12/1996 | Landry | 212/196 |
| 6,062,405 A | * | 5/2000 | Pech et al. | 212/298 |
| 6,071,062 A | * | 6/2000 | Warhurst et al. | 414/498 |
| 6,131,751 A | * | 10/2000 | Pech et al. | 212/178 |
| 6,257,165 B1 | * | 7/2001 | Danos et al. | 114/265 |
| 6,328,524 B1 | * | 12/2001 | Johnston | 414/460 |

* cited by examiner

*Primary Examiner* — Lisa M Caputo
*Assistant Examiner* — Octavia Davis
(74) *Attorney, Agent, or Firm* — Laurence A. Greenberg; Werner H. Stemer; Ralph E. Locher

(57) ABSTRACT

A mobile testing device is adjustable to perform different types of tension tests. The measuring device can conduct tests on components located on the ground or on elevated components. The measuring device can also carry out tensile strength tests on wire cables, slings, and other components. The measuring device can also be used to calibrate weight-indicating devices and instruments that indicate tensile strength. The positioning and movement of the gantry is achieved by using an assembly of hydraulic cylinders. Different working positions can thus be obtained and more than a trivial amount of physical effort is not required to operate the device.

22 Claims, 14 Drawing Sheets

MOBILE TESTING DEVICE AND METHOD OF USING THE DEVICE

CROSS-REFERENCE TO RELATED APPLICATION

This application claims the benefit under 35 U.S.C. §119 (a)-(d) of Application No. P-070100491 filed Feb. 6, 2007 in Argentina, and of Application No. 270422-07, filed Nov. 20, 2007 in Bolivia. As far as possible under the rules, the prior applications are herewith incorporated by reference in their entirety.

BACKGROUND OF THE INVENTION

1. Field of the Invention

The invention generally relates to in-situ tensile testing of components that are subjected to tensile forces, wear, and deterioration, and the invention generally relates to calibrating weight-indicating instruments. More specifically, the invention relates to a mobile testing device and to a method of using the mobile testing device to perform in-situ tensile testing of such components and to calibrate such weight-indicating instruments.

2. Description of the Related Art

A number of different industrial areas use elements or components that are subjected to tensile forces, wear, and deterioration. Such components may include, for example, wire cables, chain links, steel bars, slings, fuses, shackles, hooks, and various clamping and/or anchoring elements. When such components are regularly tested, unexpected failures of these components can be prevented.

The oil industry serves as one example of an industrial area in which it would be advantageous to test some of the many components that are subjected tensile forces, wear, and deterioration. This testing would be performed to determine the mechanical properties of these components in order to insure that such components are replaced before they deteriorate to an unreliable or dangerous state.

In the oil industry, there are a significant number of companies that are mainly concerned with lowering some sort of tool into an oil well during the lifetime of the well. A wire cable is used to lower the tool to a depth at which an operation with the tool is performed. The technical and dimensional characteristics of this wire cable are dependent upon the weight of the tool that is used. This wire cable undergoes normal wear and deterioration caused by the activity and the conditions under which it is used. Due to this wear and deterioration, the wire cable looses its mechanical properties. Therefore, it is important to regularly carry out a test to determine the minimum tensile stress, which when applied to the wire cable, will cause the wire cable to break.

If the wire cable unexpectedly breaks, the mechanical system used to lower the tool into the well cannot be used to pull the tool out. Other equipment needs to be used to fish the tool out of the well. The broken equipment, the need to use additional intervening equipment and personnel to fish out the tool, and the non-productive time during which other activities could have been performed in the oil well may all add up to a large financial loss. Such accidents can also cause physical harm to workers and/or even loss of life.

A component is under tension when evenly shared loads, which tend to cause stretching, are applied to the cross section of the component. A tensile test is best for determining the mechanical properties of several different types of components. The results of the tensile test also indicate the resistance and deformability characteristics. Therefore, by means of a simple tension state, the tensile test can determine the elastic limit, the maximum load, and the resulting static resistance values.

At the present time, a testing bench or a machine, which generally consists of one fixed jaw and one mobile jaw, is used for tensile testing wire cables, chains, slings, steel bars and other elements acting as fuses. The component to be tensioned is placed between the fixed jaw and the mobile jaw and a mechanical system applies tension to the element or component being tested. The tension can then be read from an analog or a digital tension-indicating device. This type of testing equipment is not convenient because it cannot be transported. This means that the component to be tested needs to be removed from the work-site or location of use and needs to be taken to the place where the testing equipment is located. After being placed in-use, however, it is often impractical or inconvenient to transport such components to a remote testing facility.

It is also known to use hoists to perform tensile testing on the anchors of a derrick. Using hoists, however, is generally not that safe for the personnel carrying out the test. It is also difficult to obtain the required angle using a hoist.

SUMMARY OF THE INVENTION

With the foregoing and other objects in view there is also provided, in accordance with the invention, a mobile testing device for testing a component. The mobile testing device includes: a transportable platform; a gantry supported on said platform; a system for moving said gantry from a traveling position in which said gantry is entirely supported by said platform to a testing position in which said gantry is supported on a ground surface; and a device for applying a tensile force to the component.

With the foregoing and other objects in view there is also provided, in accordance with the invention, a method of testing the component. The method includes transporting the mobile testing device to a testing location, and performing a test by applying the tensile force to the component.

The mobile testing device can be used where an in-situ tensile test is required. The mobile testing device can be used to test the tensile strength of any component that needs to be tested for safety reasons. The test may be a destructive type test to determine the breaking strength of the component being tested. The mobile testing device could also be used to perform a non-destructive test for calibrating certain weight-indicating devices, such as, for example, instrumentation gauges that function to indicate weight or tensile stress. The mobile testing device could also be used to perform a non-destructive test for determining the maximum workload that could be safely applied to certain devices, systems or components without breaking the device, system or component being tested.

The mobile testing device could be used to test wire cables and other components, such as, for example, link chains, shackles, hooks or any other element used for clamping and/or anchoring. There are also other devices, which are known as weak points, and which act as fuses to tensile stress. If the tensile stress exceeds the amount of stress that the weak point can handle, the weak point breaks and this prevents other components from being damaged. By preventing damage to these other components, a large financial loss can be prevented and the health and well being of personnel working in the field can be protected. In certain tools, the weak point is constructed by using a predetermined lesser number of strands than the total number of strands used to form other portions of the wire cable. The number of strands used to form the weak point will depend on the nature of the operation.

The well is the production focal point. During the lifetime of the well, for example, from the exploration phase to abandoning the well, the well will be intervened by different rigs in different occasions. A rig consists of several elements. One of these elements is the mast or derrick. A mechanical system is used to hang a block from the top of the derrick. In most of the operations carried out by a rig, the weight of the tool is born by this block. Through the mechanical system that holds the block to the derrick, both the weight and the stress are transferred directly to the mast. Therefore, the mast bears the following stresses: the weight of the block, the weight of the tool, the loads caused by the wind, and dynamic loads caused by the operation. These loads can make the derrick unstable and can cause an accident that produce losses in human life and health as well as in financial resources. To prevent these problems, the derrick is anchored to the ground using wire cables called guy wires. The guy wires are tied to the anchoring system itself. Generally four guy wires are provided. One guy wire is provided in each corner of the derrick. A greater number of guy wires may be used in specific situations.

The document API 4 G published by the American Petroleum Institute regulates the characteristics and the arrangement of the anchorage. The stresses that are submitted to the derrick are transferred through the guy wires to the anchorage. The anchors must be capable of resisting all of the loads that will be submitted to the mast. The load capacity of the anchors and the distance of the anchors from the bore of the well depend on the type of rig used with the well, since the dimensional and technical characteristics is dependent upon the particular rig. The rig could be, for example, a drilling rig, a workover rig, or a pulling rig. For safety reasons, the tensile strength of the anchors of the anchorage will be tested. The test specifications (tension and angle) will be directly related to the type of rig that intervenes the well.

An object of the invention is to test the tensile strength of anchors. Since the testing device is mobile, once it reaches the location where the test will be carried out, the system is ready to be completely operated in a matter of seconds. The mobile testing device is designed to easily adjust to the conditions of the test. For example, the testing angle and the applied stress are adjustable. Another advantage is that the deployable components of the mobile testing device are completely hydraulically operated. Thus, the personnel operating the mobile testing device do not have to expend any significant physical effort in order to deploy the hydraulically operated components, such as the gantry. This reduces the possibility of injury to these personnel. Once one of the anchors has been tested, the mobile testing device can be easily transported to the next anchor that will be tested. In the event that the hydraulic system fails, the gantry can be retracted to its standing position by using a manual pump. An advantage of the mobile testing device is that the period of time required to test four anchors is much less than the amount that would have otherwise been required.

An object of the invention is also to be able to calibrate numerous types of weight-indicating instruments. These instruments generally use a diaphragm-type sensor to determine weight. The diaphragm-type sensor is anchored to the master cable that is fastened to the device, for example, a traveling block or a snatch block, which is used for bringing up or down tools, pipes, etc. While tools are being run in and out of the well, the main cable is stiffened causing the diaphragm-type sensor to compress and indicate the weight on the instrument. Calibrating these weight-indicating instruments is very important because the weight being placed on the cable needs to be accurately specified. Otherwise, the cable and/or other equipment can be overloaded and this may cause an accident. If there are doubts about whether a weight-indicating instrument is working correctly, the mobile testing device can calibrate the instrument in-situ where the industrial operation is taking place. This prevents the operation from being interrupted while the weight-indicating instrument is transported, for example, from an oilfield to a remote calibrating location.

The mobile testing device can be moved to the place or area where the testing or calibration will take place and therefore enables convenient tensile testing and calibration. For example, the mobile testing device can be used to quickly determine the breaking stress at which a wire cable will collapse. After determining the breaking stress, the stress that is applied to the cable during operation in the field will be limited to a level below the breaking stress. In this manner, the cable is prevented from becoming broken from being overstressed, and economic losses and dangerous conditions for work personnel are prevented.

By keeping mobile testing device on the grounds of an oilfield, it can be moved to the exact location on the oilfield where tensile testing and/or calibrating measurements are required. After the support legs 5 are replaced with the support bar 15, the frame of the gantry can be placed in a vertical position because of the layout of the hydraulic cylinders. The hydraulic cylinders allow the frame of the gantry to be set in the position required in order to perform the testing of a component, for example, an anchor. Then the component being tested is fastened and the maximum stress that can be safely applied to the component being tested can be obtained in a few minutes.

When the support legs are used and are on the ground, an aperture angle of approximately 35° to 90° can be obtained. The angle of the gantry against a ground surface can be adjusted such that a plane extending through the frame will be at an angle of 35 to 90 degrees with respect to the ground surface.

The gantry can also operate against a vertical surface. In this case, the maximum height at which it can correctly operate is at 2.5 m. The angle of the gantry against a vertical surface can be adjusted such that an aperture angle will be at an angle of between 35 and 180 degrees with respect to the ground surface. A large number of direct or indirect tensile tests are possible due to the number of different positions in which the gantry can be placed.

It is common to locate a weak point in the connection between the tool and the wire cable in wire line equipment, for example, perforation and logging equipment or slick line equipment (equipment to measure and regulate the flow rate in secondary recovery). This weak point is usually formed by using a smaller number of strands than the number of strands that are used to form the other portions of the wire cable. The object of this weak point is to prevent the wire cable from collapsing at undesirable points, which would result in undesirable complications.

To determine the tensile strength of the weak point using the mobile testing device, a clamping bolt is placed in the eye of the bar. This clamping bolt is then fastened to the lower end of the wire cable, and the upper end of the wire cable is clamped to the eye of the pulling or tension cylinder. The tensile strength of the weak point is determined by activating the tension cylinder to apply a stress until the wire cable breaks.

With regard to safety, there is a considerable distance between the element being tested and the operator. There is also a protection mesh that prevents a possible accident.

DETAILED DESCRIPTION OF THE INVENTION

Figure 1:
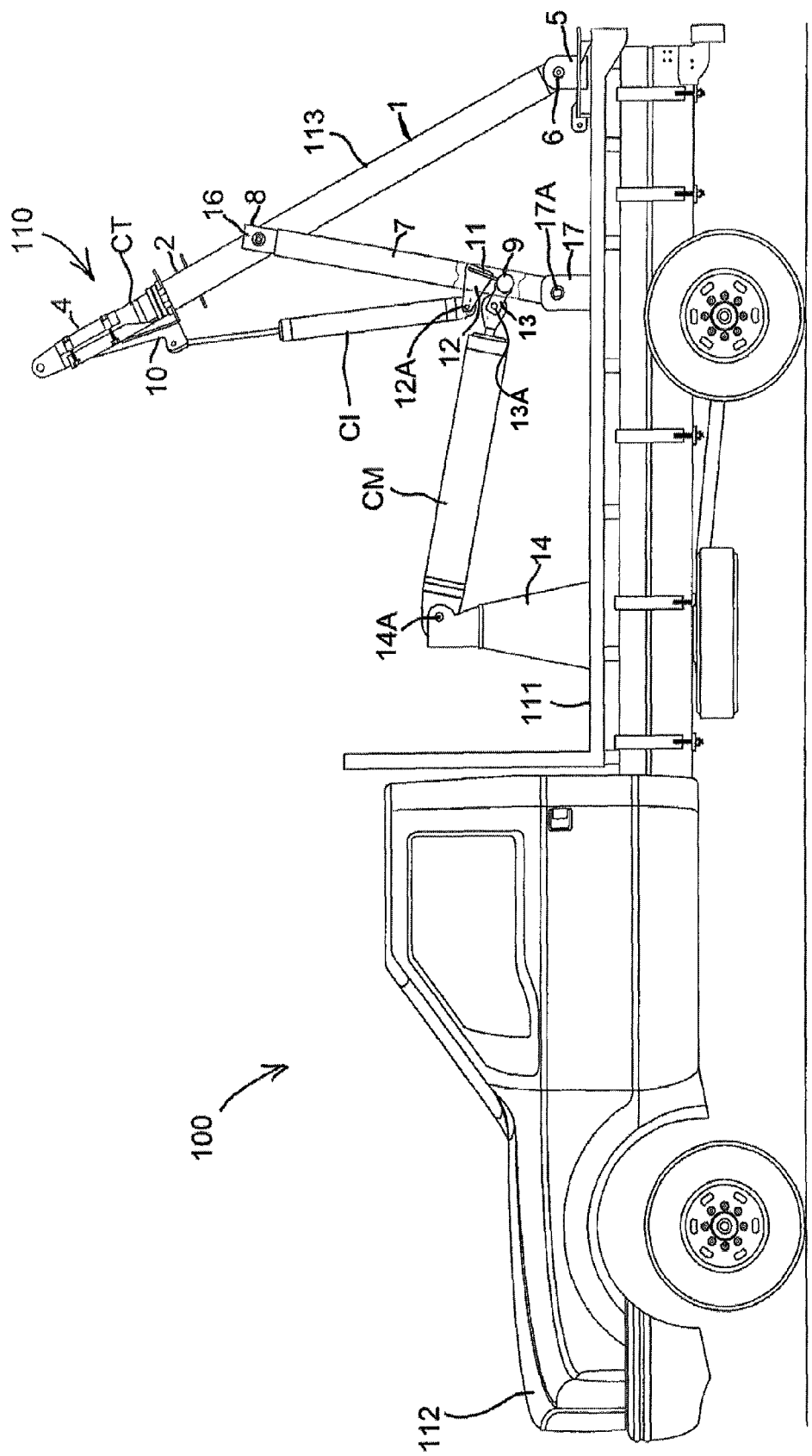
FIG. 1 is a side view of a mobile testing device in a traveling position.

Referring now to the figures of the drawing in detail and first particularly to FIG. 1 thereof, there is shown a side view of a mobile testing device 100 in which the components thereof are set in a traveling position. The mobile testing device 100 includes a folding gantry 110 that is constructed on a moveable platform 111. The moveable platform 111 could be formed as part of a wheeled trailer or could be part of a motor vehicle. In the exemplary embodiment, the moveable platform 111 is shown as the rear bed of a suitably sized truck 112 that satisfies the required load capacity. The gantry 110 is formed from two spaced apart UPN type steel beams 1. Since FIG. 1 is a side view, only one of the beams 1 can be seen.

Figures 2A, 2B:
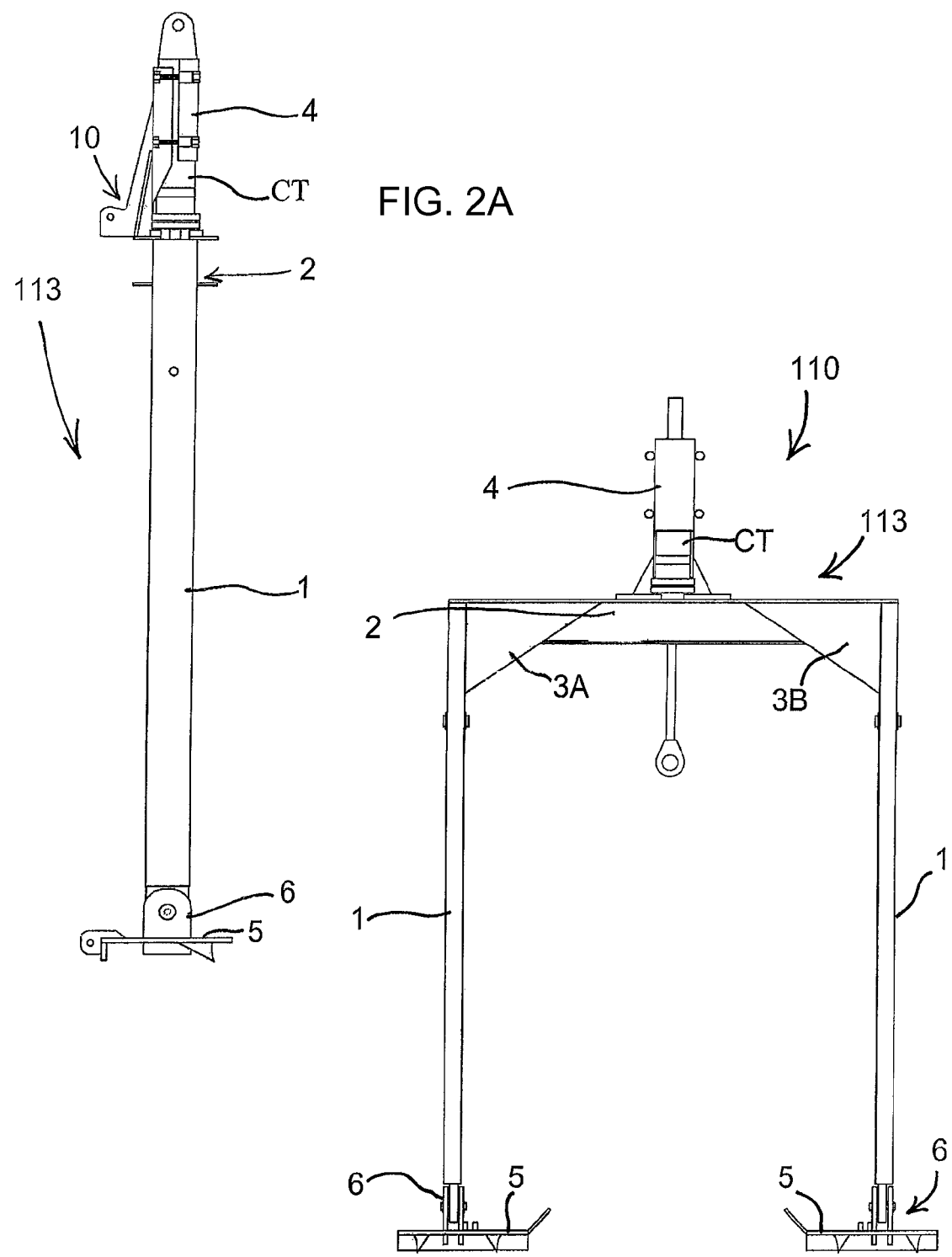
FIG. 2A is a side view of the frame.
FIG. 2B is a rear view of the frame.

As can be seen in FIG. 2B, the gantry 110 includes a frame 113 and each of the beams 1 forms a column of the frame 113. FIG. 2A is a side view of the frame 113 and FIG. 2B is a rear view of the frame 113 (Note that components connecting the frame 113 to the platform 111 are not shown in FIGS. 2A and 2B; these components will be discussed later). FIG. 2B shows that the frame 113 of the gantry 110 also includes a lintel 2 that extends horizontally between the beams 1. The lintel 2 is preferably made from two UPN type steel beams. The frame 113 of the gantry 110 includes a rigidity plate 3A located at the rear left side of the frame 113 and a rigidity plate 3B located at the rear right side of the frame 113. Although not shown in the drawings, rigidity plates are similarly located at the front left side of the frame 113 and at the front right side of the frame 113. The beams 1, the lintel 2, the illustrated rigidity plates 3A and 3B, and the non-illustrated rigidity plates cooperate to support a tension cylinder CT that is located on the upper side of the lintel 2.

FIGS. 2A and 2B show a saddle-type chamber 4 that holds the tension cylinder CT. The lintel 2 is configured to allow the piston rod of the tension cylinder CT to operate freely without touching the piston rod. This prevents the lintel 2 from interfering with testing that will be performed with the tension cylinder CT. A group of ribs is distributed inside the lintel 2 in order to give the structure a greater grade of rigidity without loosing the elasticity necessary for the operation.

FIGS. 2A and 2B also show that a respective articulated connection 6 connects a support leg 5 to each beam 1 at the lower end of the frame 113. The articulated connections 6 and the geometry of the support legs 5 cooperate to rapidly achieve mechanical balance by evenly distributing the tensile stresses through the beams 1 and then properly transmitting the tensile stresses to the ground surface.

Referring again to FIG. 1, a respective extendable lifting arm 7 is located at each outer side of the frame 113 of the gantry 110 to connect the frame 113 to the platform 111. Only one such arm 7 can be seen in the side view of FIG. 1. These arms 7 are made from properly reinforced steel rectangular pipes. One end of each of the arms 7 includes a telescopic unit 8 so that the arms 7 can be extended to provide a larger distance between the gantry support point 16 and the platform 111. The arms 7 allow the frame 113 of the gantry 110 to be appropriately inclined if required by the topographic conditions of the ground surface. The tilting cylinder CI is used to extend the telescopic unit 8 of the arms 7. The cylinder piston of the tilting cylinder CI is connected between the arms 7 and the gantry 110.

A wing 10 is constructed above the lintel 2 on the gantry 110. This wing 10 extends perpendicular to the chamber of the pulling or tension cylinder CT (Also see FIG. 2A). One end of the tilting cylinder CI is connected to the wing 10 by a through bolt that permits free movement. The other end of the tilting cylinder CI is anchored to the arms 7.

Figure 2D:
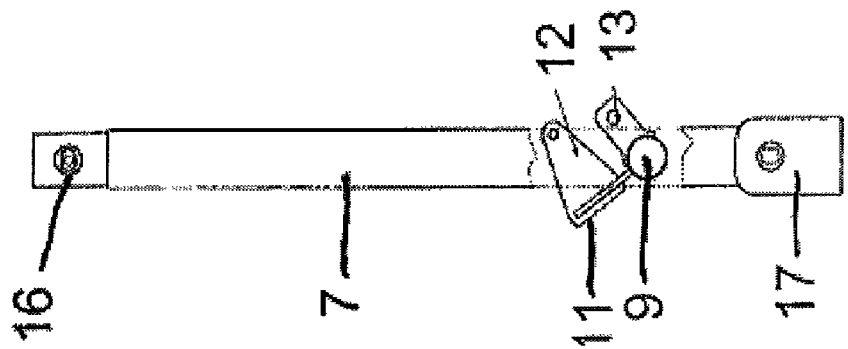
FIG. 2D is a side view of the lifting arms and associated connections.
Figure 2C:
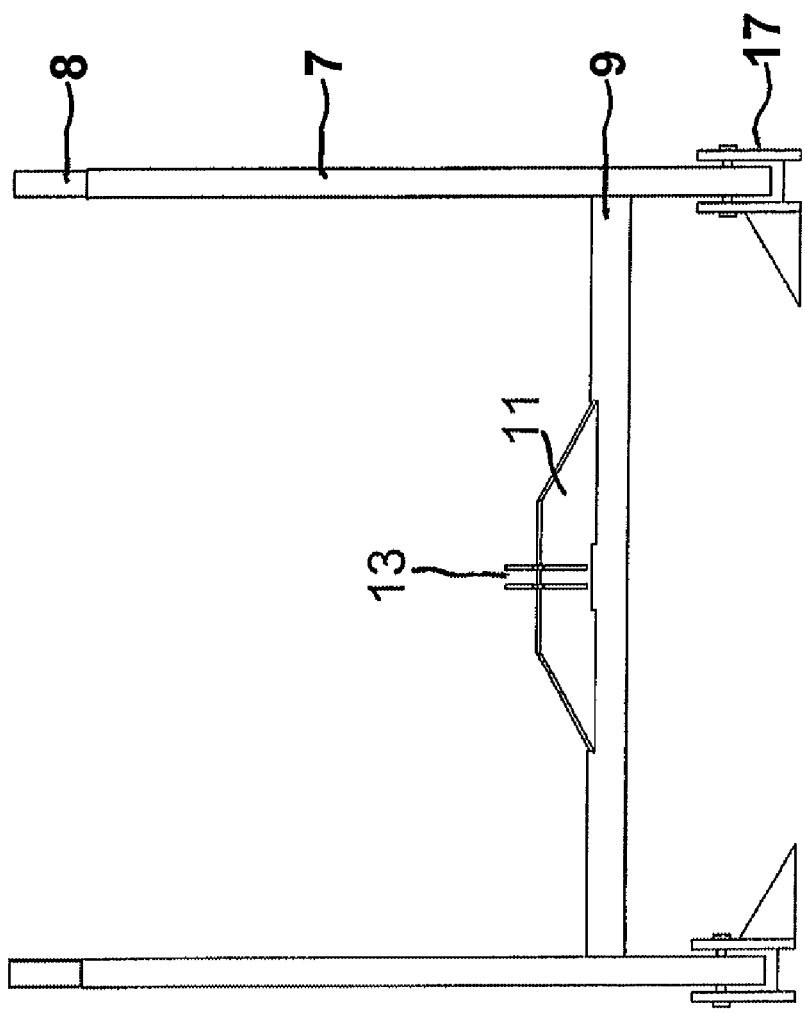
FIG. 2C is a rear view of the lifting arms and associated connections.

FIG. 2C is a rear view of the arms 7 and FIG. 2D is a side view of the 7 arms. Note that these figures have been drawn without showing certain other cooperating features of the mobile testing device 100. A crossbar 9 connects the lower end of the arms 7 together. A trapezoidal cantilever 11 is placed on the central part of the crossbar 9. The trapezoidal cantilever 11 functions to provide support and clearance.

As can be best seen in FIG. 1, the trapezoidal cantilever 11 supports an eye 12 that holds the tilting cylinder CI. A through bolt 12A connects one end of the tilting cylinder CI to the eye 12. The through bolt 12A allows rotation of the tilting cylinder CI about the longitudinal axis of the bolt 12A. The trapezoidal cantilever 11 functions to provide a clearance by separating the point of connection of the tilting cylinder CI from the plane formed by the parallel arms 7. The gantry 110 can then be moved in a circular manner about the gantry support point 16. Bolts are used to provide the necessary articulation about the gantry support point 16.

A connection eye 13 is connected to the crossbar 9 at an angle of 90° with respect to the cantilever 11. A through bolt 13A cooperates with the connection eye 13 to form an articulated connection with an end of the rod of the master cylinder CM.

A prism-shaped structure 14 holds the other end of the master cylinder CM above the platform 111. A through bolt 14A cooperates with the prism-shaped structure 14 to form an articulated connection with that end of the master cylinder CM. The prism-shaped structure 14 is configured to allow that end of the master cylinder CM to perform an angular movement of just a few grades with respect to a line parallel with the ground.

The arms 7 function to position and move the frame 113 of the gantry 110. The arms 7 do not absorb stresses during the tensile test because the gantry 110 absorbs all of these stresses. The bottom of each arm 7 is connected to the platform 111 by an articulated joint 17 enabling the arm 7 to rotate around the longitudinal axis of a cooperating through bolt 17A. Each joint 17 can include a plate located on each side of the tubular structure of an arm 7.

The linear movement of the rod of the master cylinder CM moves the arms 7. Since there is a large distance between the connection eye 13, which is connected to the rod of the master cylinder CM, and the gantry support point 16, the thrust of the rod of the master cylinder CM is converted to an adequate torque having an action point at the central axis of the crossbar 9. The forward and backward movement of the rod of the master cylinder CM produces the upward and downward movement of the gantry 110.

Figures 7A, 7B:
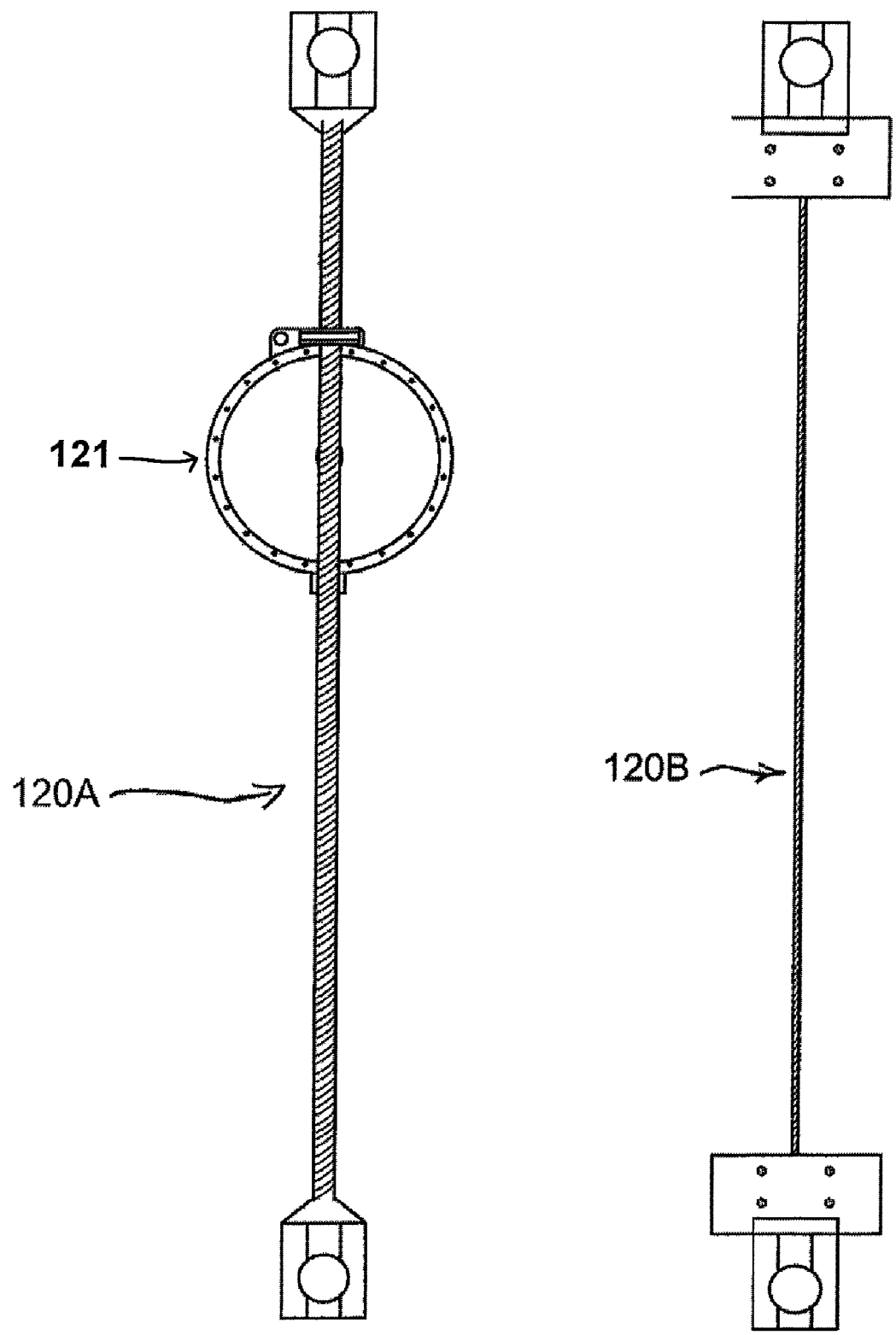
FIG. 7A shows a cable that can be attached to a weight-indicating instrument.
FIG. 7B shows a cable that will undergo a weak point test.

Three hydraulic cylinders CM, CI, CT have been described. The master cylinder CM functions to enable the vertical positioning of the frame 110 of the gantry 110. The tilting cylinder CI functions to enable the telescoping movement of the arms 7 and to adequately tilt the frame 110 of the gantry 110. A clamping device may be connected to the anchor so that the tension cylinder CT can apply a tension to the anchor. FIG. 7A shows a cable 120A that can be used to attach the tension cylinder CT to a weight-indicating instrument in order to apply tension to the weight-indicating instrument. The circular component is a load sensor diaphragm 121. FIG. 7B shows a cable 120B undergoing a weak point test. A jaw could also be used for performing a weak point test.

Figure 3:
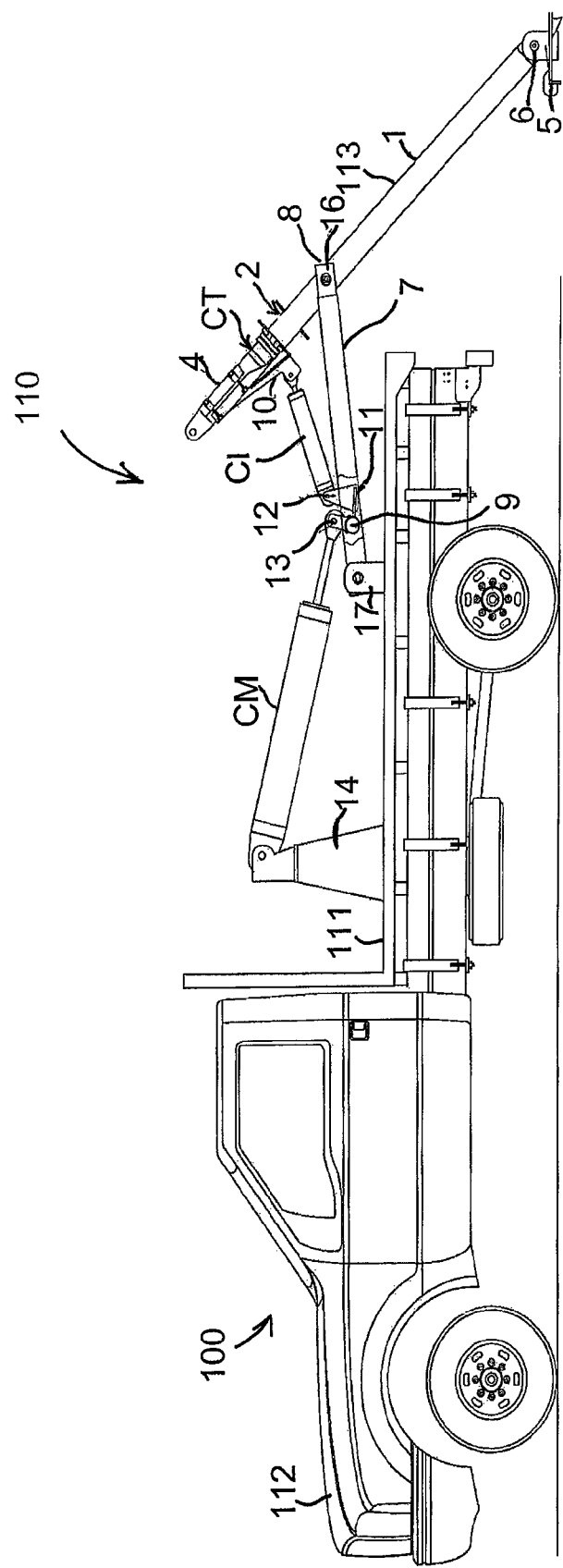
FIG. 3 is a side view of the mobile testing device showing the gantry in one possible position against the ground.
Figure 4:
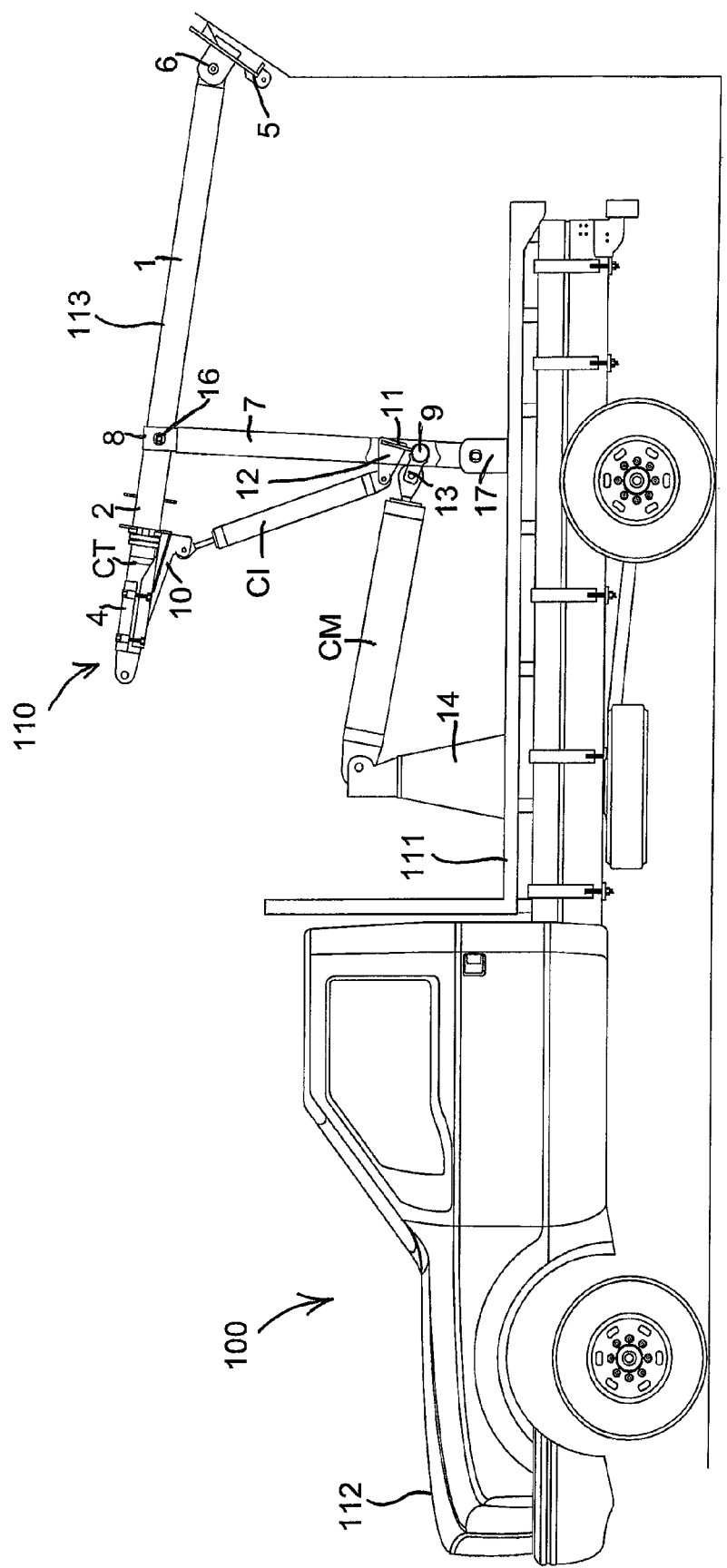
FIG. 4 is a side view of the mobile testing device showing the lifting arms in a position substantially perpendicular to the ground.

FIG. 4 is a side view of the mobile testing device 100 showing the gantry 110 being moved through a position in which the arms 7 are substantially perpendicular to the ground. The bottom of the gantry 110 will be moved towards the ground as the hydraulic cylinders CM, CI, CT continue to be actuated. The three hydraulic cylinders CM, CI, CT, which have already been described, are double-effect cylinders. FIG. 3 is a side view of the mobile testing device 100 showing the gantry 110 in one possible position against the ground.

Figure 13:
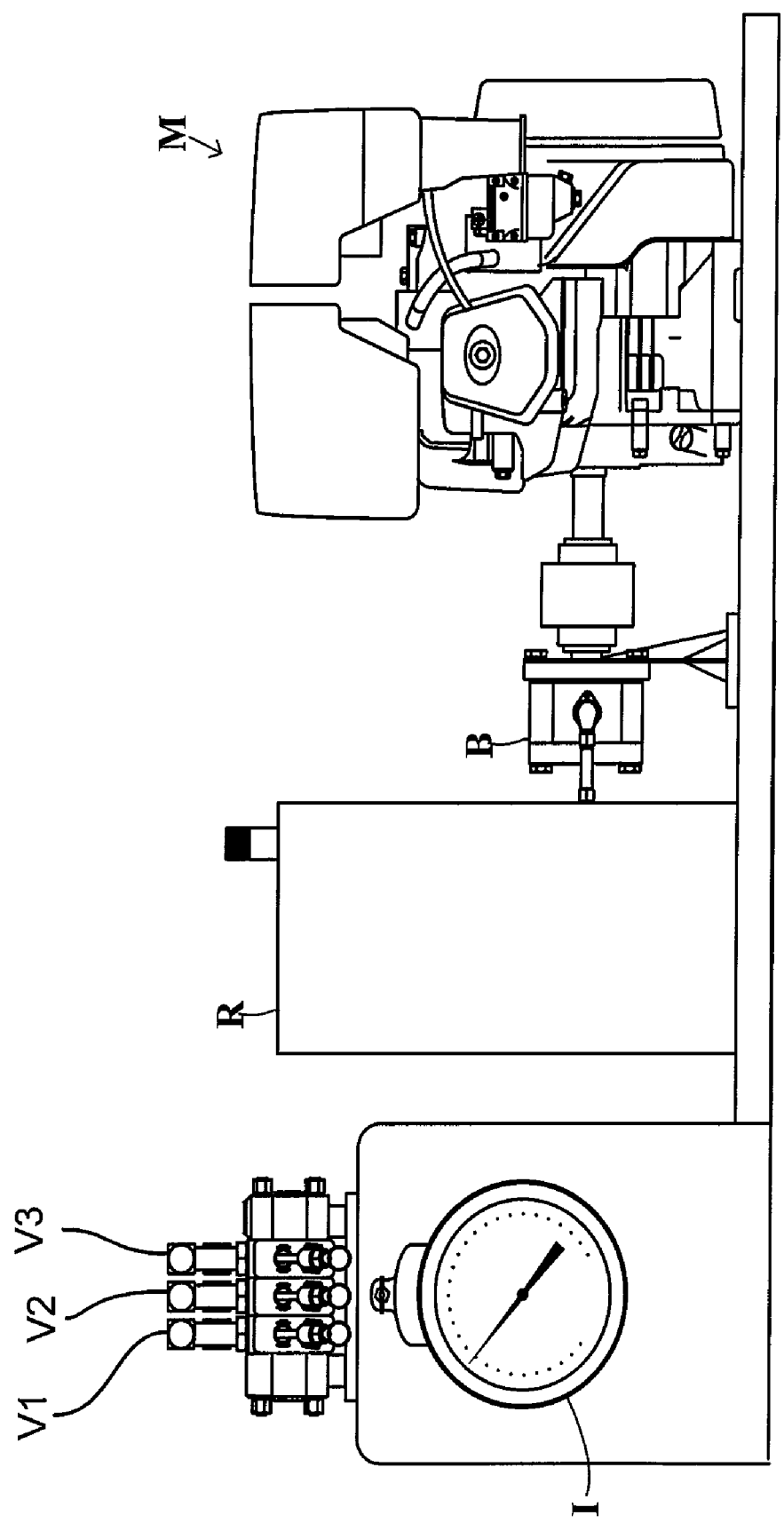
FIG. 13 shows additional components of the hydraulic system.

FIG. 13 shows additional components of the hydraulic system. These components have not been illustrated in the side views of the mobile testing device 110 so that other features could be clearly illustrated. Three hand-control valves V1, V2, V3 produce the forward and backward movement of the hydraulic cylinders CM, CI, CT. The work pressure and flow rate are produced by a hydraulic geared pump B which takes the hydraulic fluid from a reservoir R and compresses it until the required working pressure is obtained. An internal combustion engine M drives the pump B. The hydraulic system is connected through hoses. A control pressure gauge I can be provided in order to constantly check the working pressure of the hydraulic system. The components shown in FIG. 13 can be placed on the moveable platform 111, for example, near the prism-shaped structure 14 such that the engine M fits under the master cylinder CM.

For safety reasons, a non-illustrated protection mesh may be provided on the upper part of the gantry 110. This mesh will protect the operator in case a clamping device breaks during the tensile test and an element is ejected.

Figure 12:
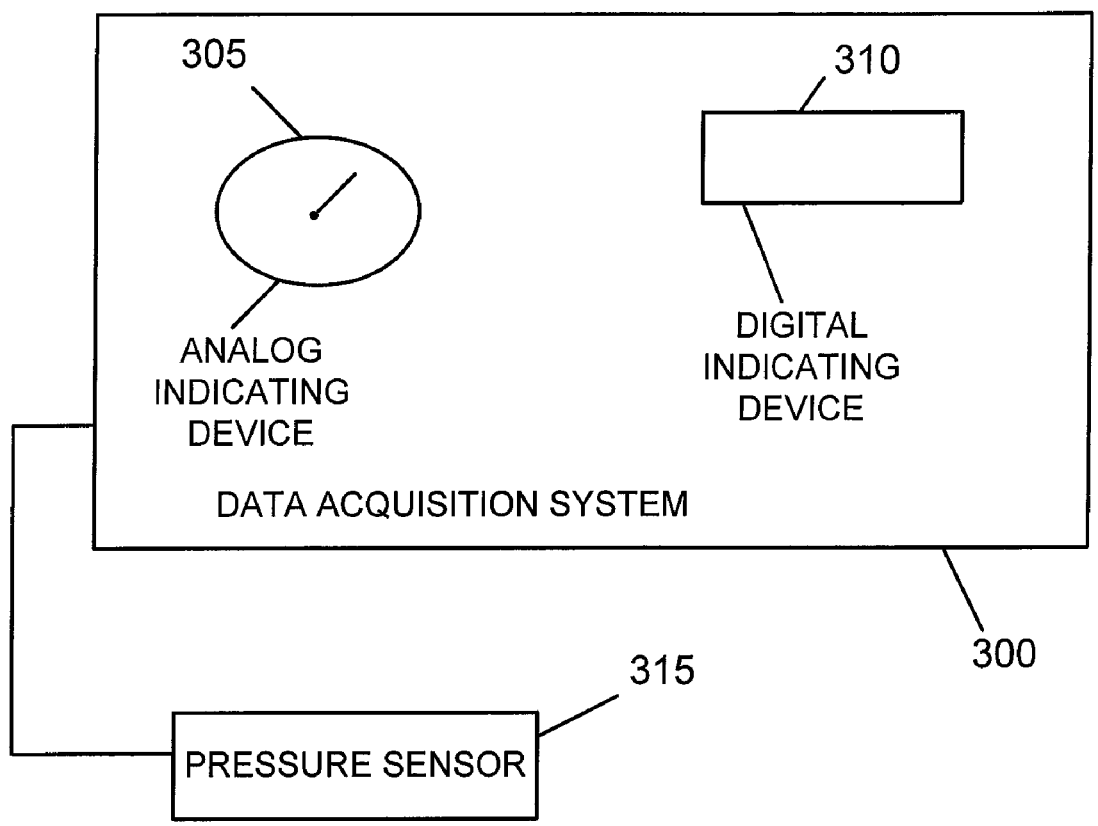
FIG. 12 shows a data acquisition system.

FIG. 12 shows a data acquisition system 300 including two tension-indicating devices 305, 310 may be provided for verifying the stress that is applied to an anchor during a test. An analog tension-indicating device 305 can show and read the pressure in the tension cylinder CT. The pressure is directly read in tons since the dial of the instrument is corrected by a coefficient that considers the effective section of the cylinder in the upstroke. A digital tension-indicating device 310 includes a transducer that converts the analog signals into digital electrical signals. The data acquisition system 300 performs adequate sampling and processes the sampled signal to produce a temporal reading of the tensile strength. Appropriate hardware is used to provide out a real time reading and interpretation of the test being conducted. The data acquisition system 300 also includes a pressure sensor 315 capable of sensing 0-1000 bars or even a larger value, a data acquisition board, and appropriate software. The data acquisition system 300 may be constructed separately from the mobile testing device 100 and brought to the testing site along with the mobile testing device 100. Alternatively, the data acquisition system 300 may be constructed as an integral part of the mobile testing device 100.

Figure 5:
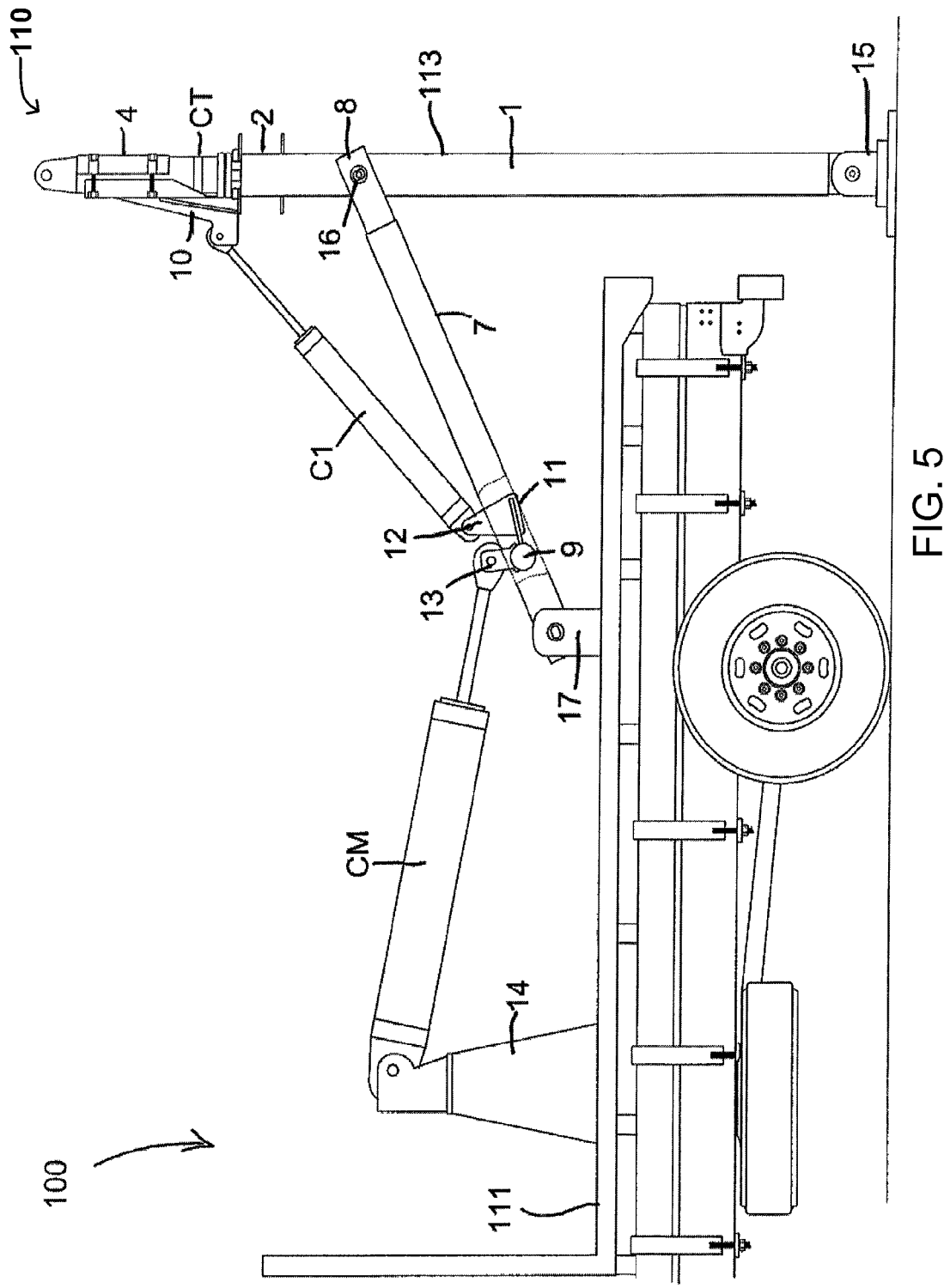
FIG. 5 is a partial side view of the mobile testing device shown in a position suitable for performing tensile tests and calibration operations.
Figure 6:
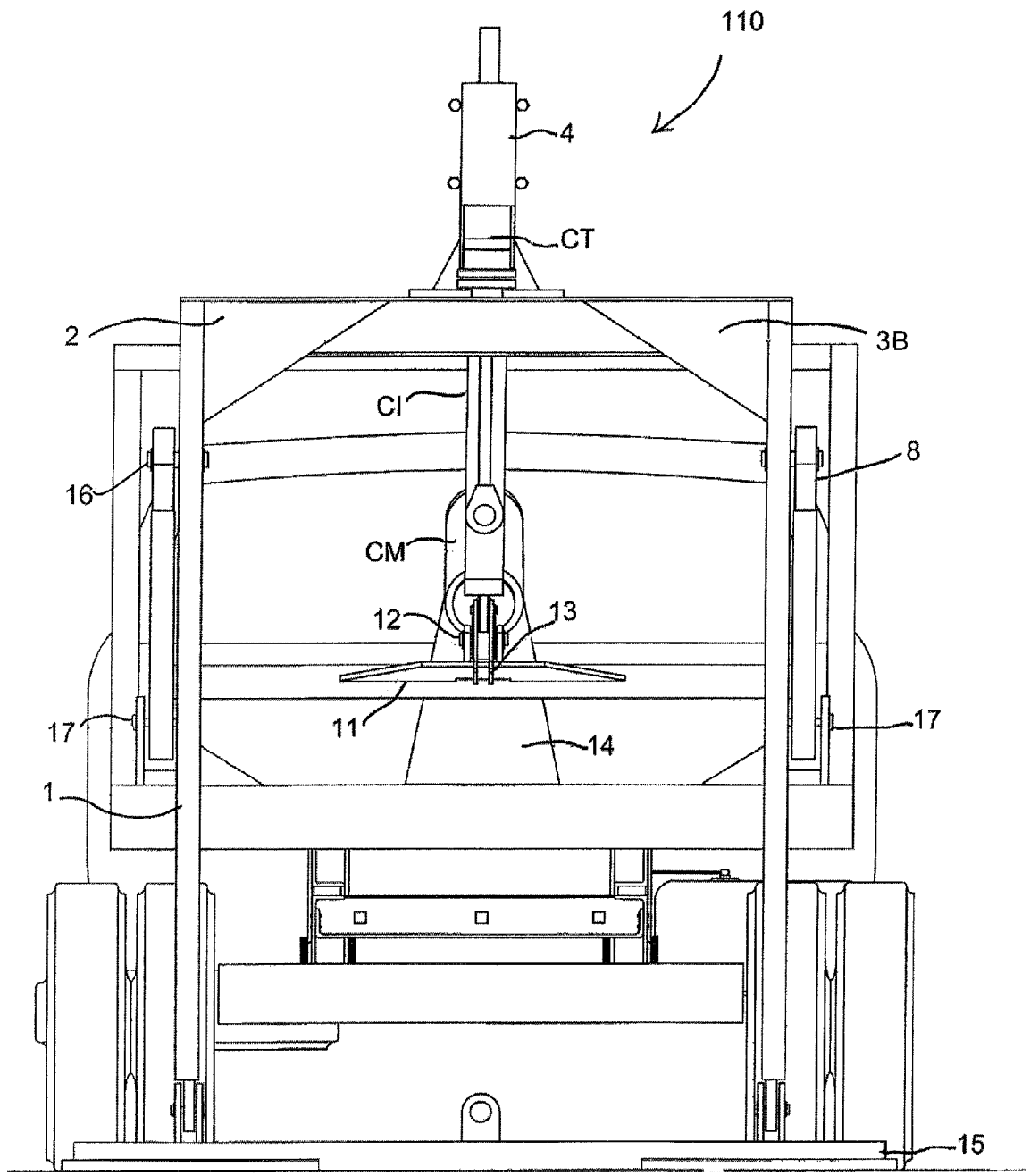
FIG. 6 is a rear view of the mobile testing device in the state shown in FIG. 5.

The support legs 5 together with the telescopic unit 8 of the arms 7 are used to test the anchors of oilrigs. FIG. 5 is a partial side view of the mobile testing device 100 shown in a position suitable for performing tensile tests and calibration operations. A diaphragm-type sensor or hydraulic load cell is suitable for performing these tests and/or calibrations. In FIG. 5, each of the support legs 5 has been removed and has been replaced by a support bar 15 that is fixed to the beam 1 by a clamping bolt. The mobile testing device 100, as shown in FIG. 5, is suitable to run a tension test of any element. If this is the case, the plane of the frame 113 of the gantry 110 will be placed in the vertical position at an angle of 90° with respect to the ground surface. FIG. 6 is a rear view of the mobile testing device 100 in the state shown in FIG. 5.

Initially, the mobile testing device 100 will be in the traveling position as shown in FIG. 1. For safety reasons, fast-activation butterfly-type joints and through bolts are used to fix the support legs 5 to the moveable platform 111 while the mobile testing device 100 is being transported from the operational base to the field. After the mobile testing device 100 arrives at the remote location in the field, the butterfly-type joints and bolts are loosened so that the support legs 5 are no longer fixed to the moveable platform 111.

After the support legs 5 have been released, the internal combustion engine M is activated to activate the hydraulic geared pump B. The hydraulic system will reach satisfactory working conditions in a few seconds. The master cylinder CM is activated to move the crossbar 9, and this movement is transferred to the arms 7, which move the gantry 110. This is possible because at this point in time the gantry 110 is in a fixed position with respect to the arms 7. The tilting cylinder CI provides the stiffness that fixes the position. The support legs 5 of the gantry 110 are now suspended at a height above the ground that is sufficient to enable work personnel to replace the support legs 5 with the support bar 15 without requiring a lot of physical effort. The support legs 5 will be used to test anchors. The support bar 15, however, will replace the support legs 5 and will be used to perform breaking and weak point tensile tests.

The following procedure will be performed if the operational test that will be performed is verifying and/or determining the cable breaking strength, verifying and/or determining weak point stress, or calibrating weight-indicating instruments. After the support bar 15 has been fixed to the gantry 110 using bolts and is placed in a working position, the support bar 15 is laid on the ground. The element that will be tested is fastened to the tensiometer in a manner depending on the test that will be performed. When performing a calibration between the lower eye bar and the upper eye-pulling cylinder, a steel cable portion will be used to simulate the main cable. Then, the tensiometer will be set on the cable. After the one of the hand-control valves V1, V2, V3 that drives the tension cylinder CT is actuated, the cable will be increasingly pulled out. The resulting data both in the analog tension indicating device and in the digital tension indicating device are compared so that the instrument calibration is as precise as possible.

If the test being performed is a breaking point test or a weak point test, the only variation will be in the connection of the components to be tested. With respect to anchor tests, either in oilrigs or in communication towers, the clearance between the beams 1 forming the columns of the gantry 110 should be sufficient such that the beams 1 do not interfere with the anchor positioning. After determining the distance from the anchor to the wellbore and consequently, the stress to be applied during testing, the mobile testing device 100 is positioned and the master cylinder CM is activated. The master cylinder CM can move freely somewhat parallel to the ground surface. Then, the tilt of the gantry 110 is adjusted to the required testing position. The master cylinder CM presses the frame 113 against the ground to prevent an undesired displacement during the test. The tension cylinder CT is activated and the rod of the tension cylinder CT is fully extended. Passing the pull element through the rod of the tension cylinder CT and through the eyes of the anchor fastens the anchor. Once this pull element is fastened, the tension cylinder CT is set for upstroke. During operation, the analog and digital tension indicating devices develop, control and record the tensile stress that is obtained. The digital data is stored in the memory of the data acquisition system 300 and a copy of the data is given to the customer.

The mobile testing device 100 can be used for performing many different procedures, which may include, for example, certifying guy wire anchors in oilrigs, tensile testing, and calibrating weight-indicating instruments. The documents API 4G, API 9A, and API 9B published by the American Petroleum Institute may be used as reference material relating to certifying anchors. API 4G Recommended Practices for Maintenance and Use of Drilling and Well Workover Structures, API 9A Specification for Wire Cable, and API 9B Recommended Practice on Application, Care, and Use of Wire Cable for Oilfield Service are hereby incorporated by reference in their entirety. API 9A Specification for Wire Cable may also be used as reference material relating to tensile testing.

The documents ISO ISO 9001:2000 Standard—Section 7.1 Planning of Product Realization, and IRAM 301:2000 Standard—Section 5.4 Test and Calibration Methods and Method Validation are also hereby incorporated by reference in their entirety. These two documents may be used as reference material relating to calibrating weight-indicating instruments. Reference can also be made to the Quality System Manual published by Petroil S.R.L.

Some background information will now be given before describing the procedure for certifying the guy wires of the anchors in oilrigs. An anchor is an assembly formed by a sling or a wire cable that has, for example, a diameter of one inch, and a portion of pipe of a length and diameter determined by the technical requirements. One of the commonly used dimensional configurations has a pipe of a length of 1.8 meters with a diameter of 9 inches. This pipe is located in a fixed position underground and has the guy wires of the derrick fastened thereto. A wire cable is an assembly of helically laid wires forming a metal cable that is able to resist tensile stresses and that has appropriate flexibility qualities. The wire cable is formed by three basic components: the wires forming a strand, a plurality of strands, and the core. The arrangement of these components varies in order to produce cables with specific characteristics that are suitable for specific purposes.

The procedure for certifying guy wire anchors in oilrigs is divided into two stages—a visual inspection and a pulling test, which applies tensile forces to the anchors. By performing a visual inspection, many defects can be found. The most common defects that can be found by performing a visual inspection include, for example, the following: a deformation inside the strands as a result of a torsional unbalance during use; a collapse in the core resulting from the application of excessive stress; a wire break among the strands; a wire break due to fatigue; a protrusion of the core due to shock-loading; mechanical damage resulting from movement of the cable over a sharp edge; evidence of corrosion in one or several strands forming the cable; and localized wear and deformations as a result of a previous shock in the cable. If another type of defect is found, the characteristics of the defect can be recorded so that a further analysis can be performed to determine the possible cause of the defect.

It is also preferable to check the following additional items. The distance from the upper end of the sling cable to the lower end of the cable that is on the ground surface can be inspected. One can also check whether appropriate signage is in place. For example, whether fluorescent orange tape made of Polyethylene terephthalate and sold under the name Dacron™ is in place. Information relating to the surface of the connecting cable sling can also be determined. For example, one may determine whether the surface of the connecting cable sling is underground, is on the ground with a length that does not exceed the cable dimensions, is on the ground with a length that is equal to or less than one meter beyond the cable dimensions, or is on the ground with a length of more than one meter beyond the cable dimensions.

One may check whether the cable-ferrule has been provided with an appropriate asphalt paint coating. One may check whether the ground characteristics at the anchorage location allow for proper fluid drainage out of the ground. One may check the type of eye termination, for example, whether there is a ferrule secured or leaden bottle type termination. One may check the wire cable type (for example, a diameter of 1 inch, 6×36 WS AFS). One may check the cable pattern (for example, F1-GU-0).

Figure 9A:
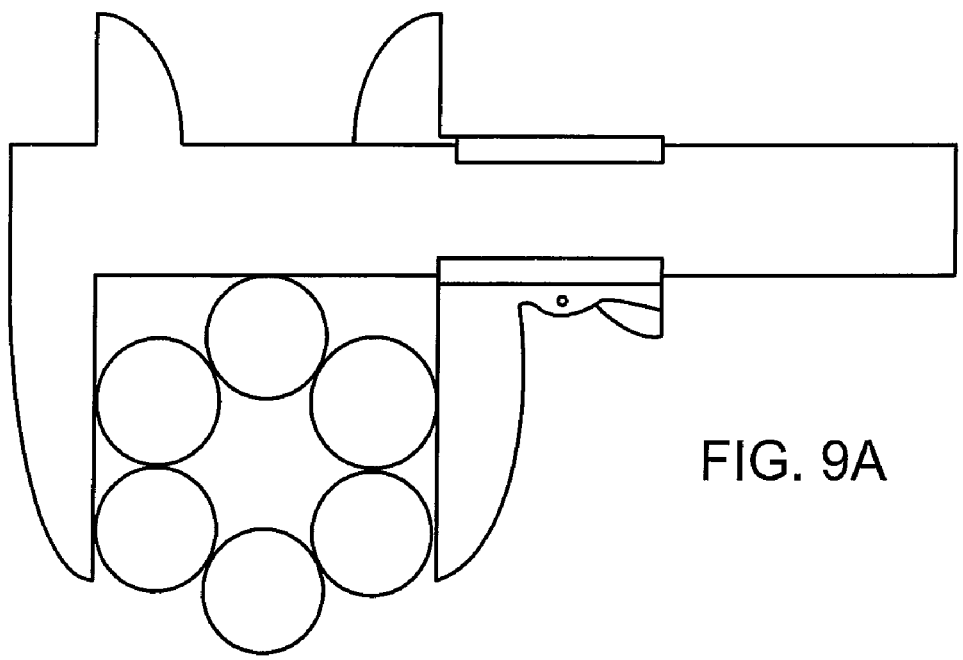
FIG. 9A shows manual measurements being incorrectly taken of the diameter of a cable.
Figure 9B:
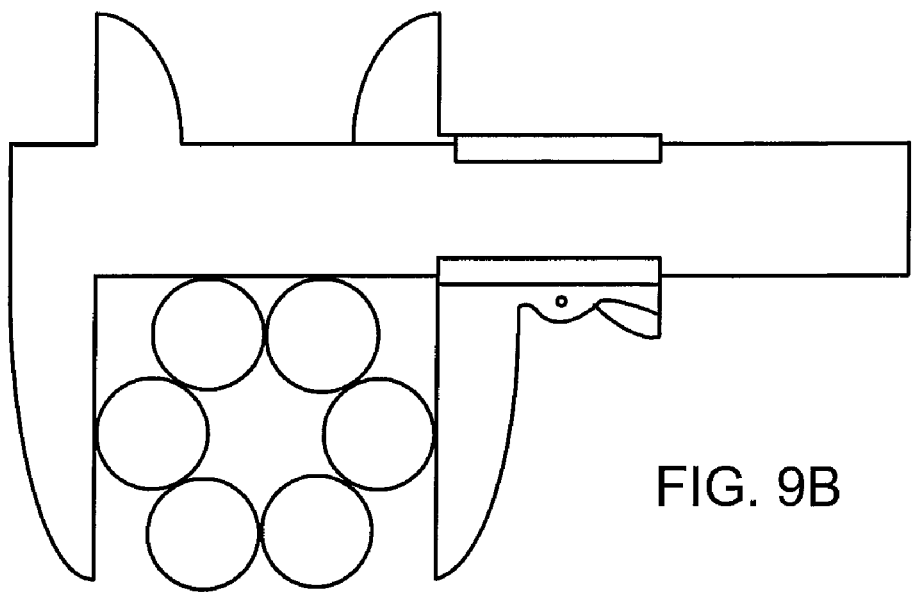
FIG. 9B shows manual measurements being correctly taken of the diameter of a cable.

The visual inspection of guy wire anchors in oilrigs preferably includes several steps and these steps will now be described in detail. First, if necessary, the ferrule or bottle of the cable termination is adequately cleaned so that the identification number can be seen and so that the anchor can be clearly identified. The identification number can be used to keep appropriate records relating to the anchor. It can be appropriately noted if this identification number is not present. This applies for eyes with this specific termination. Next the cable diameter is measured. This measurement is preferably taken during every regular inspection and this measurement can be recorded for future comparisons. This measurement is correct only when it is taken between the wire crowns that constitute the strand. FIG. 9A shows the measurement being taken in an incorrect manner. FIG. 9B shows the measurement being taken correctly between the widest points of the cable.

The diameter of the cable may be reduced as a consequence of several factors, for example, initial stretching, normal wear, and internal deterioration of the strand. The reduction due to initial stretching is why it is necessary to take and record a first measurement. Outer cables, especially those on the crown of the strands will show normal wear. When the strand core starts deteriorating it is first revealed by a reduction in the diameter. If the diameter reduction is excessive, the inside of the strand should be examined.

It is preferable to verify the torsion type of the cable prior to the first time that the cable is subjected to a load so that the torsion type can be used for subsequent comparisons. The torsion type is the length required by a strand to spiral or to give one turn around the core. There are two aspects related to the cable torsion. First, the lay direction is related to the cable torsion, i.e. left or right. The second aspect refers to the relative position of the wires in the strand and of the strands in the cable. In regular lay cables, the wires are laid in the opposite direction to the strands in the cable. In Lang Lay cables, the wires and strands have the same lay direction. Changes in the strand length necessary to cover the core are a result of the gradual deterioration of the wire cable. An abrupt change indicates another kind of problem. As a rule, if stretching is observed in the lay along with a reduction in the cable diameter, one can suspect that core destruction or an internal collapse has occurred. The unlay is the result of a torsion in the opposite direction to the natural one of the cable. The reason for the unlay can be recorded for reference during future inspections.

The type of cable and the type of pattern used to construct the cable are identified during the visual inspection. Wire cables are identified by a nomenclature that indicates the number of strands, the number of wires in each strand, the type of construction, and the core type. A descriptive letter indicates the type of construction. These letters are: S—Seale; W—Warrington; F—Filler; and WS—Warrington-Seale. The core type is indicated by AT—Textile core; AA—Steel core; and AF—Fiber core. The pattern of the cable is indicated by the following nomenclature: F—the number of legs; O—simple eye; and Gu—thimble. One possible pattern is F1-GU-O, for example. Another possible pattern is F1-O-O, for example.

The strand of the cable is preferably internally inspected. The strand can be opened so that it can be internally inspected without damaging the strand. A pointed tool, such as, for example, a Phillips screwdriver, may be used for this purpose. The pointed tool can be placed through two strands and can be turned so that the core is visible. In the case of IWRC strands, the point where the strands make contact with the core can be inspected for defects. If strands with broken wires are found this has likely been caused by contact with adjacent strands or with the IWRC. The core can be inspected for damaged fibers. If small pieces of fiber, less than ¼" long, for example, come out of the core, this may sometimes indicate overloaded points. After testing, the cable can be returned to its standing condition.

After the anchor has been visually inspected, the anchor will be pull tested by applying tensile forces to determine the tensile strength of the anchor. The distance between the anchor and the bore of the well is measured over the perpendicular to the diagonal having ends at the anchors adjacent to the anchor that will be tested. The center of this diagonal passes over the well bore. After this measurement, the tensile stress will be applied to the tested anchor to determine whether the anchor can handle the tensile stress. The value of the stress that will be applied will be taken from the location drawing that specifies the anchor distribution and the anchor capacity. Each anchor must have a minimum verified capacity of at least twice the load that will be supplied to the anchor by the guy wire.

The pulling test will now be described. The pull will be carried out at an angle similar to that of the guy wire in the direction of the anchor towards the center of the well. The testing stress will be applied for at least two minutes after the movement of the anchor has stopped. The data acquisition system 300 (See FIG. 12) will be used when performing the pull test. The data acquisition system 300 includes a pressure sensor capable of sensing 0-1000 bars or even a larger value, a data acquisition board, and appropriate software.

The mobile testing device 100 will be located at an appropriate distance from the anchor so that the frame 113 of the gantry 110 can be correctly positioned on the ground, assuming that this positioning is possible in a way that will not affect the quality of the test. After the mobile testing device 100 is appropriately located, the bolts and butterflies fixing the gantry 110 to the platform 111 will be loosened. The internal combustion engine M will be started and the hand-control valves V1, V2, V3 that control the hydraulic cylinders CI, CT, and CM will be activated.

First, the tilting cylinder CI will lift the frame 113 of the gantry 110, which will then be laid down by the master cylinder CM. The tilting cylinder CI will also be used to set the intended angle. If the frame 113 of the gantry 110 cannot be placed at the intended angle, the ground surface should be conditioned using a shovel without hitting or damaging the anchor.

Figure 8:
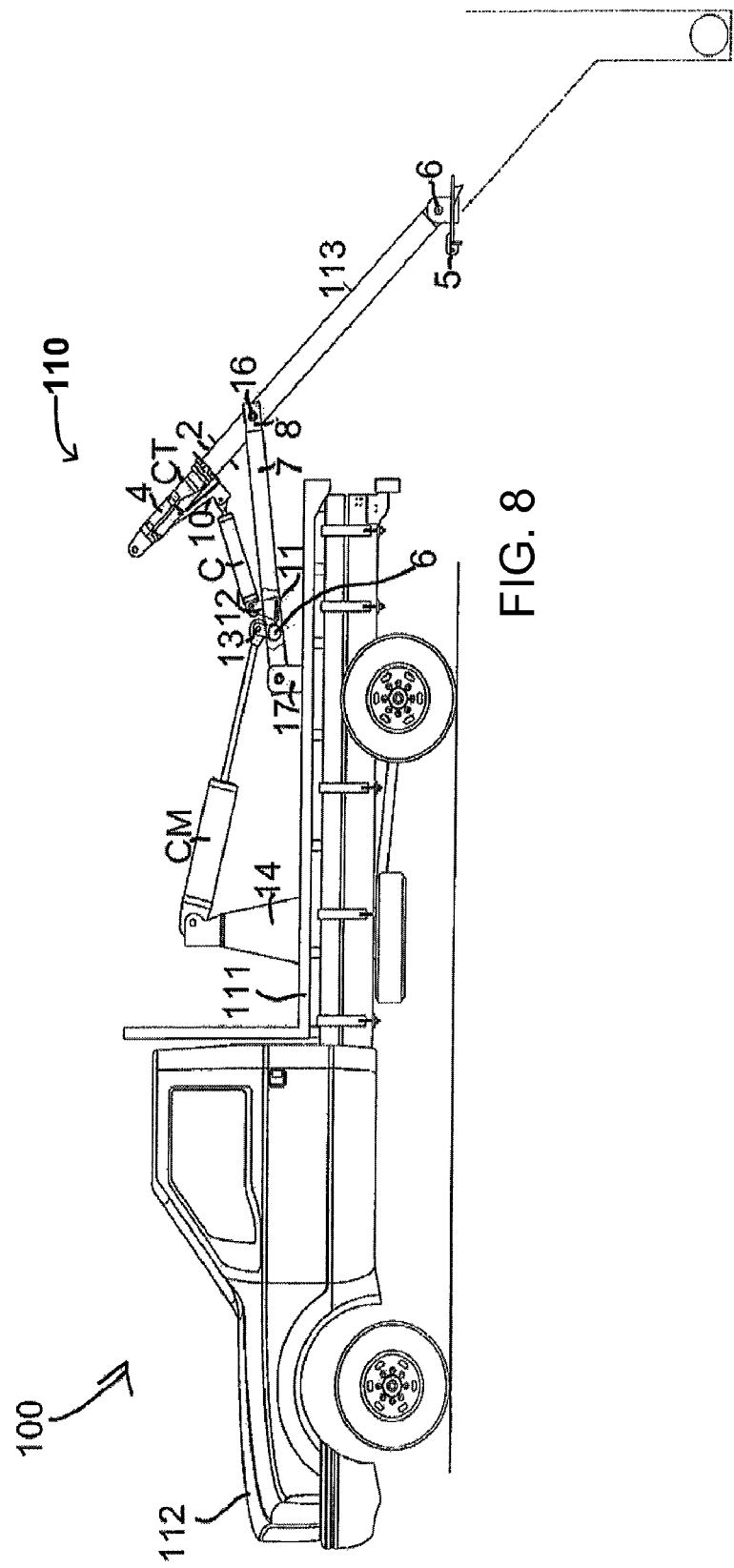
FIG. 8 is a side view of the mobile testing device running a tensile test in a rig anchorage.
Figure 11:
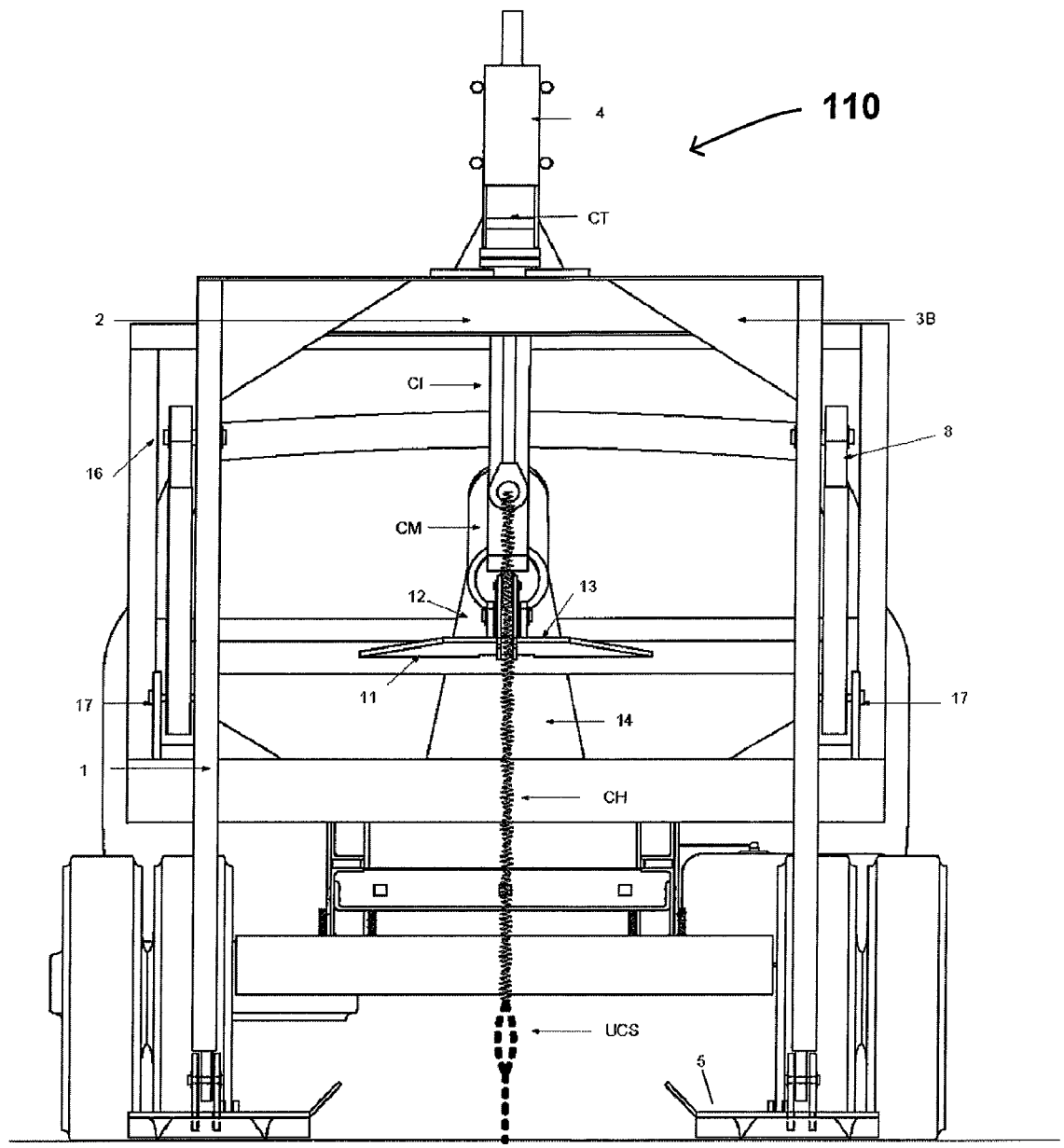
FIG. 11 is a rear view of the mobile testing device in a position for performing another test.

FIG. 8 is a side view of the mobile testing device 100 running a tensile test on a rig anchor. FIG. 11 is a rear view of the mobile testing device 100 in a position for performing a test of an anchor UCS. The support legs 5 will be placed so as to allow the upper connecting cable sling to be perpendicular to the tension cylinder CT. Once ready to commence the testing, a chain CH and appropriate fittings or elements will be used to fasten the eye of the anchor UCS to the pulling eye of the tension cylinder CT.

The elements employed to attach the eye of the anchor UCS and eye of the tension cylinder CT may include, for example, a clevis grab hook that is used for shortening the length of the chain dependent upon the distance between the eye of the anchor UCS and the eye of the tension cylinder CT. The chain CH passes through the eye of the tension cylinder CT. If the anchor UCS does not have an eye, then shackles may be used for attachment purposes. Depending upon the particular circumstances, other elements may be needed to connect the tension cylinder CT to the anchor UCS.

The data acquisition system 300 will be connected and the previously determined stress will be applied to run the test. If this stress value is not obtained in the first attempt, the fastening will be adjusted and another attempt will be made. Failure to reach the desired stress value in the first test is a direct consequence of the position of the anchor. For example, a new standing position will be obtained after the cable stretches. If the testing stress cannot be maintained for at least two minutes after trying several fastening operations, if it becomes clear that the cable length with respect to the ground surface consecutively increases, and if the volume of loose soil on the ground surface progressively increases as well, the anchor does not to meet the minimum requirements and it will not be approved. This routine will be repeated with all of the anchors. If the anchor arrangement is not symmetrical (the anchors are not equidistant with respect to the wellbore), the testing stress that is applied to all of the anchors will be set to correspond to the stress that is transferred to the anchor that is nearest to the wellbore during operation. Thus, the highest stress will be applied to all of the anchors.

The operating procedure for tensile testing cables, slings and chains will now be described. As previously mentioned, a wire cable consists of three basic components whose patterns vary to produce cables with specific characteristics and purposes. The three basic components are the wires forming a strand, a plurality of strands, and a core. In cables used for slick line or wire line operations, the core consists of an assembly of conductor copper wires that provide communication between the tool that is being used and the acquisition equipment or system. The number of electrical conductors will vary according to the operational requirements of the customer. These electrical conductors are electrically isolated from the wire cable by some kind of a synthetic coating.

A visual inspection is performed before the tensile test. The cable that will be tensile tested will be adequately cleaned if required. The cable diameter will be measured and recorded at every periodic inspection of the cable being tested. The degree of wear of the cable can be determined by measuring the diameter of the cable. The diameter is measured in two octagonal planes. One of the planes should be perpendicular to the cable axis. When the cable is worn, the measured diameter will be less than the original cable cross-section. The measured diameter should be close to the original cable diameter. If the reduction in the wire diameter exceeds 20%, the wear is severe and replacing the cable should be considered. When measuring the cable cross-section, the cable can be checked for the presence of foreign particles that may affect the actual diameter.

There are two cable types that are available to the operator, which do not vary in their basic construction characteristics. These are wire cables for general purposes and for specific purposes. Wire cables for specific purposes include those used in wire line and in slick line operations. These two cable types will have various diameters and various numbers of conductors.

The most common defects that result from cable service operations include mechanical damage resulting from movement of the cable over a sharp edge, evidence of corrosion in one or more strands that form the cable, and the formation of a bird cage indicating shock loading.

All wires constituting the cable are zinc coated for a better protection. The presence of white rust zinc oxide indicates that the zinc coating has deteriorated and that the cable must be cleaned and lubricated. When red rust iron oxide has formed, it indicates that the zinc is seriously affected and that the steel base is being attacked. This attack may turn into pitting which, if not treated, will result in a failure of the steel wires. When deterioration signs have been found, periodic examinations of the cable should be carried out.

One of the evaluations that the operator in charge of the test must perform is the "e" test. For this purpose, a series of wires, of about 18"-24" long, must be individually removed from the cable. The operator will hold one of the cable ends and form a loop, which will be turned into an "e"-shape. If, while conducting the test, the wire breaks, the cable should be removed from service.

In general, the condition of the wire zinc coating indicates wear or the need for correction. When a wire exhibits pitting that exceeds 6% of the diameter, it must be rejected. If other defects are found, their characteristics should be recorded so that in the future, an analysis of the possible causes can be performed.

When performing a tensile test on a sling, a similar visual inspection as that described above for cables should be performed. When performing a tensile test on a chain, one should check the initial length and the link diameter. One should also check for deformations of the chain perpendicular to the operational direction.

After the cable, sling or chain has been visually inspected, it will be pull tested by performing a tensile test. A breaking and/or weak point test can be performed. This test determines the breaking strength or weak point of the component. Stress is applied to the component until there is a collapse. For example, stress can be applied to the wire line and the slick line until there is a collapse in the cable or the weak point. By means of the applied tension, this type of testing helps determine whether the working stress is within the established parameters. If, while carrying out this test, the tested component breaks, the tested component does not meet the operational requirements. The value of the applied stress is recorded.

The pulling test will now be described. The support legs 5 that are used during transportation are removed and replaced by the support bar 15. Then the gantry 110 is located perpendicular to the ground. In order to perform the breaking and/or weak point test, first a sample is taken from the cable being tested and the sample is anchored to the tension unit using clamps. Care should be used to insure that the clamps do not exert compression stress on the cable. Such compression stress may deteriorate the cable and consequently affect the breaking strength of the cable. Each one of the ends of the cable will be anchored to the corresponding eye used as a tension element. In the weak point test, the lower end of the cable with the weak point will be fastened with jaws. In both cases, the pull stress will be applied in an axial way with respect to the cable, thus ensuring that tensile stresses are correctly transmitted to the cable. The applied testing stress will be increased until the cable collapses. The component to be tested will be fastened appropriately in order to prevent undesired deviations.

The test is digitally performed using a pressure sensor of 0-1000 bars, a data acquisition board, and appropriate software. A multiplier will be used since this is a pressure data acquisition. The value of the multiplier corresponds to the effective flat section of the pulling piston. The tensile stress will then be read in lbf.

Figure 10:
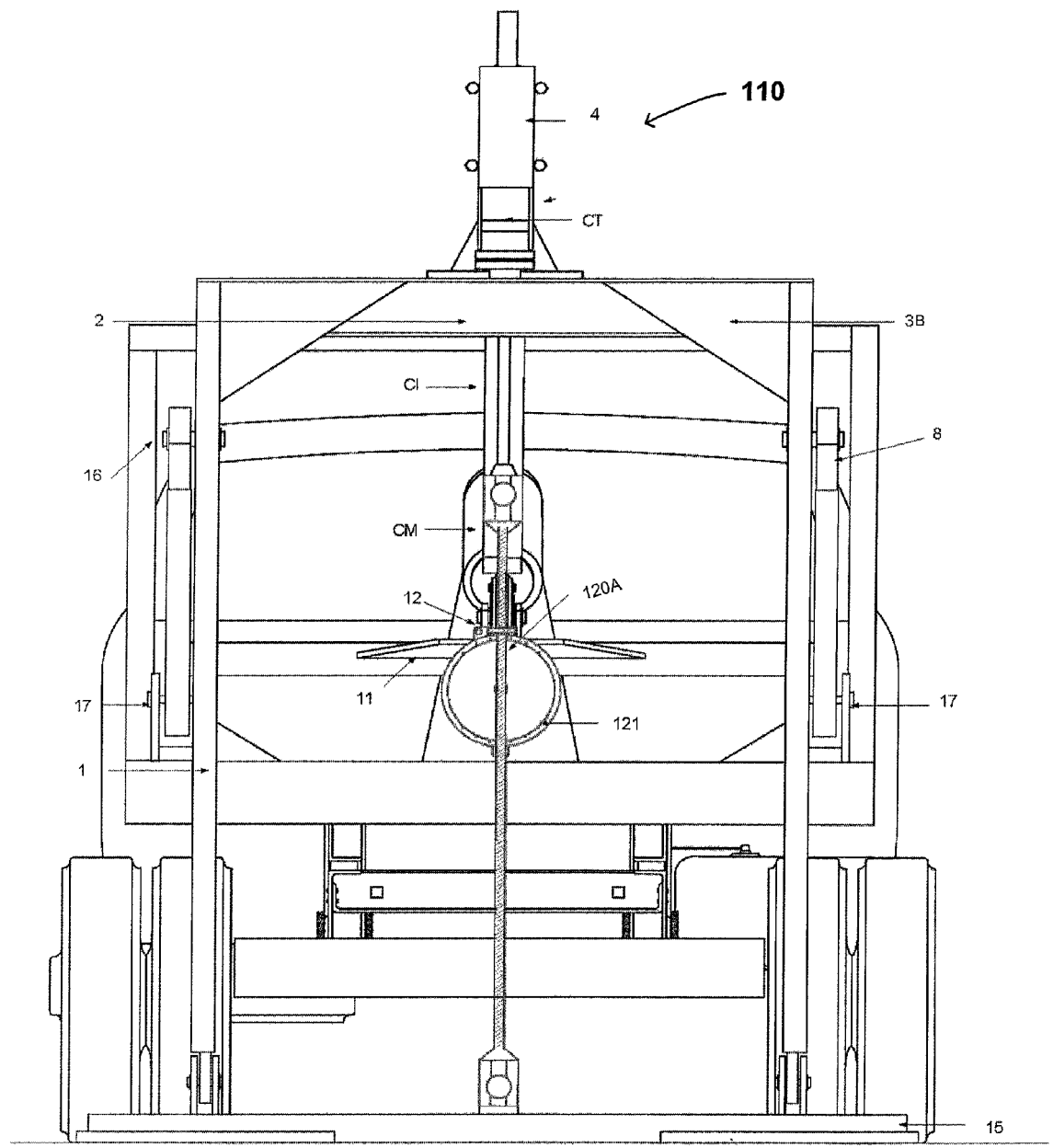
FIG. 10 is a rear view of the mobile testing device in a position for calibrating a weight-indicating instrument.

FIG. 10 is a rear view of the mobile testing device 100 in a position for calibrating a weight-indicating instrument. the procedure for calibrating weight-indicating instruments will now be explained. after the mobile testing device 100 is at the location where the weight-indicating instrument that will be calibrated is located, all necessary information for identifying and tracking the weight-indicating instrument is recorded. such information can include, for example, the trademark, dial, type of instrument, and/or rig to which the instrument belongs. then, the general condition of the weight-indicating instrument is checked. each particular type of instrument will have different characteristics to be considered, but in general, during the calibration it is necessary to verify the condition of the bourdon tube dial, the display, the connections, and the linkeys.

Should deterioration of some component be found during the general verification, the defect is first corrected on the testing bench, the connectors are adjusted, and calibration relating to the Bourdon tube and the final pressure, which is direct pressure, is started. The instrument forward and rewind linkeys are used to approximate the calibration to the standard value. When this approximation is not possible, the Bourdon tube should be replaced. Even when there is only a 3% deviation, the Bourdon tube should be replaced. A 0-1000 pound full-scale test is performed for 15 minutes to check the sensor, which transmits the output signals, for breaking and/or stretching. In case breaking and/or stretching is found, the disc should be replaced. Calibration cannot generally be performed at full scale due to the operating magnitude of some instruments. Consequently, calibration is conducted at the lower range of the instrument and then it is extrapolated to the upper range.

The invention claimed is:

1. A mobile testing device for testing a component, the mobile testing device comprising:
   a transportable platform;
   a gantry supported on said platform;
   a system for moving said gantry from a traveling position in which said gantry is entirely supported by said platform to a testing position in which said gantry is supported on a ground surface; and
   a device for applying a tensile force to the component undergoing testing.

2. The mobile testing device according to claim 1, wherein:
   said system for moving said gantry includes a hydraulic system with at least one hydraulic cylinder moving said gantry from a traveling position to a testing position.

3. The mobile testing device according to claim 1, wherein:
   said system for moving said gantry includes a hydraulic system with a plurality of hydraulic cylinders moving said gantry from a traveling position to a testing position.

4. The mobile testing device according to claim 1, wherein:
   said device for applying the tensile force to the component is a tension cylinder.

5. The mobile testing device according to claim 1, further comprising:
   a vehicle for moving said platform.

6. The mobile testing device according to claim 5, wherein:
   said platform is a part of said vehicle.

7. The mobile testing device according to claim 1, wherein:
   said gantry includes a plurality of articulated support legs that support said gantry from underneath said gantry while said device applies the tensile force the component undergoing testing; and
   the component undergoing testing is an anchor.

8. The mobile testing device according to claim 1, wherein:
   said gantry includes a support bar for supporting said gantry while applying the tensile force to the component.

9. The mobile testing device according to claim 1, wherein:
   said system for moving said gantry includes a plurality of telescopic arms increasing a distance between said gantry and said platform, a crossbar extending between said plurality of arms, a cantilever located on said crossbar, an eye located on said cantilever, and a tilting cylinder supported by said eye; and
   said cantilever and said eye separate said tilting cylinder from a plane extending through said plurality of arms by a distance enabling a sufficient torque to be produced to move said gantry.

10. The mobile testing device according to claim 1, wherein:
    said gantry has a longitudinal length and said gantry includes a frame extending along said longitudinal length;
    said system for moving said gantry adjusts an angle of said gantry against a ground surface such that a plane extending through said longitudinal length of said frame will be at an angle of 35 to 90 degrees with respect to the ground surface; and
    said system for moving said gantry adjusts an angle of said gantry against a vertical surface such that an aperture angle will be at an angle of 35 to 180 degrees with respect to the ground surface.

11. The mobile testing device according to claim 1 in combination with the component, wherein:
    said gantry includes a frame including two UPN type steel columns and a plurality of support legs;
    said frame of said gantry absorbs internal stresses that are produced when applying the tensile force without loading said system for moving said gantry; and
    the component is an anchor being pull tested.

12. The mobile testing device according to claim 1, wherein:
    said gantry includes a frame including two UPN type steel columns and a support bar;
    said frame of said gantry absorbs internal stresses that are produced when applying the tensile force without loading said system for moving said gantry.

13. The mobile testing device according to claim 1, wherein:
    said system for moving said gantry includes a plurality of telescopic arms increasing a distance between said gantry and said platform;
    said plurality of arms being connected between said gantry and said platform.

14. The mobile testing device according to claim 13, wherein:
    said system for moving said gantry includes a master cylinder, an eye connected to said master cylinder, a bolt extending through said eye, and a crossbar rigidly connecting said plurality of arms; and
    said crossbar, said eye, and said bolt cooperating to form an articulated connection between said master cylinder and said plurality of arms.

15. The mobile testing device according to claim 1, wherein:
    said system for moving said gantry includes a master cylinder having an end, and a prism-shaped structure supporting said end of said master cylinder above said platform.

16. The mobile testing device according to claim 1, further comprising:
    a tension indicating device for indicating the tensile force applied to the component by said device for applying a tensile force.

17. A method of testing, comprising:
    providing a mobile testing device for testing a component, the mobile testing device including:
      a transportable platform,
      a gantry supported on the platform,
      a system for moving the gantry from a traveling position in which the gantry is entirely supported by the platform to a testing position in which the gantry is supported on a ground surface, and
      a device for applying a tensile force to the component undergoing testing;
    transporting the mobile testing device to a testing location; and
    performing a test by applying the tensile force to the component.

18. The method according to claim 17, wherein:
    the component is a guy line anchor.

19. The method according to claim 17, wherein:
    the component is a cable, a sling or a chain.

20. The method according to claim 17, wherein:
    the component is a weight-indicating device; and
    the tensile force is applied to the weight-indicating device to repair, calibrate, install and/or maintain the weight-indicating device.

21. The method according to claim 17, wherein the test is selected from the group consisting of:
    a verification test to verify a breaking strength or weak point stress of the component, a determination test to determine a breaking strength or weak point stress of the component, and a calibration test to calibrate the component when the component is a weight-indicating instrument.

22. A mobile testing device for testing a component, the mobile testing device comprising:

a transportable platform;

a gantry supported on said platform;

a system for moving said gantry from a traveling position in which said gantry is entirely supported by said platform to a testing position in which said gantry is not located on said platform and is supported on a ground surface; and a device for applying a tensile force to the component undergoing testing while said system keeps said platform in said testing position in which said gantry is not located on said platform and is supported on the ground surface.

* * * * *